(12) United States Patent
Dharan et al.

(10) Patent No.: US 7,144,857 B2
(45) Date of Patent: Dec. 5, 2006

(54) VANCOMYCIN HAEMOSTATIC PASTE COMPOSITION

(76) Inventors: Murali Dharan, 5401 Norris Canyon Rd., Suite 202, San Ramon, CA (US) 94583; Ronald Wasserman, 500 Hunsaker Canyon Rd., Lafayette, CA (US) 94549; Adolph Valdez, 1608 Highland Ct., Fairfield, CA (US) 94534

(*) Notice: Subject to any disclaimer, the term of this patent is extended or adjusted under 35 U.S.C. 154(b) by 0 days.

(21) Appl. No.: 10/758,548

(22) Filed: Jan. 15, 2004

(65) Prior Publication Data

US 2005/0159342 A1 Jul. 21, 2005

(51) Int. Cl.
*A61K 38/14* (2006.01)
*A61K 38/00* (2006.01)

(52) U.S. Cl. ............................... 514/8; 514/2
(58) Field of Classification Search .............. None
See application file for complete search history.

(56) References Cited

U.S. PATENT DOCUMENTS

2004/0052841 A1* 3/2004 Vogt et al. .................. 424/468

OTHER PUBLICATIONS

Winkler et al., 2000, Journal of Antimicrobial Chemotherapy, vol. 26, pp. 423-428.*

Halasz, Nicholas A., Wound infection and topical Antibiotics, The Surgeon's Dilemma, Arch Surg, vol. 112, Oct. 1977 pp. 1240-1244.

Vander Salm, Thomas J., et al., Reduction of sternal infection by application of topical vancomycin, J Thorac Cardiovasc Surg 1989; 98: 618-22.

* cited by examiner

*Primary Examiner*—B. Dell Chism
(74) *Attorney, Agent, or Firm*—Eric G. Masamori

(57) ABSTRACT

A haemostatic paste composition comprising powdered vancomycin mixed with a biocompatible carrier. The haemostatic paste composition is easily handled, adheres to a cut bone surface or an exposed bone surface, provides for effective haemostasis to prevent blood loss from a cut bone surface or an exposed bone surface, has no systemic or local adverse effect and provides bacteriostatic and bacteriocidal protection. The haemostatic paste composition is well suited for use with sternotomy incisions, but can also be used for any cut bone surface or exposed bone surface during surgery.

7 Claims, No Drawings

VANCOMYCIN HAEMOSTATIC PASTE COMPOSITION

FIELD OF THE INVENTION

This invention relates to a haemostatic paste composition. More specifically, a haemostatic paste composition comprising powdered vancomycin mixed with sterile water, aqueous saline solution or other biocompatible carrier that is easily handled, adheres to a cut bone surface or an exposed bone surface, provides for effective haemostasis to prevent blood loss from a cut bone surface or an exposed bone during surgery and has no systemic or local adverse effect. The invention also provides protection by being bacteriostatic or bacteriocidal.

BACKGROUND OF THE INVENTION

Doctors and medical professionals have used a variety of substances to control bleeding from cut bone surfaces. Typical materials used for the control of this type of bleeding are bone wax, collagen, oxidized cellulose and thrombin. However, each of these well-known materials has drawbacks in its use as a haemostatic composition. Furthermore, none of these well-known materials possess antibacterial properties.

Bone wax, typically made from a combination of refined beeswax and a softening agent, is brittle at room temperature and requires heat for proper handling. Furthermore, bone wax does not adhere well to cut bone surfaces and is neither biodegradable nor antibacterial. Bone wax is a foreign material that is not readily absorbed by the body, which may interfere with bone regrowth or become a nidus for bacterial contamination.

Collagen is a white, water insoluble fiber typically derived from bovine corium collagen. Collagen has inherent haemostatic properties mostly due to the helical structure of the collagen protein and is absorbed by the body. However, collagen powder is difficult to handle since the powder or fibers stick to wet gloves and form a gel thereon making application to the wound site difficult. Collagen sponges are effective hemostats but do make intimate contact with the wound site. The consistency is too soft for optimal application.

Oxidized cellulose is a solid composition which is soluble in fluids from wounds, forming a sticky mass which readily adheres to wound surfaces. The body absorbs oxidized cellulose. However, oxidized cellulose is insoluble in water and it is reported that moistening with water or saline reduces the haemostatic properties of oxidized cellulose.

Thrombin is a well known clotting agent, but may cause allergic reactions in some individuals. Thrombin also requires mixing with another agent, such as cryoprecipitate or calcium, and also requires a carrier medium. Thrombin has no antibacterial effect.

The use of vancomycin as an antibiotic agent is well known. Vancomycin is a tricyclic glycopeptide antibiotic which interferes with bacterial cell wall synthesis in multiplying microorganisms. Vancomycin is active against gram-positive bacteria, such as Streptococci, Staphylococci, Clostridia, Corynebacteria and Listeria monocytogenes. Vancomycin is particularly used in the treatment of severe staphylococcal infections where other antibiotics cannot be used due to patient intolerance or bacterial drug resistance. Commercially available powdered vancomycin is typically reconstituted in sterile water and the resulting solution is administered intravenously.

Prophylactic topical vancomycin has been proven to prevent sternal wound infections in individuals undergoing median sternotomy for cardiac surgery. Topical antibiotics have been demonstrated to achieve much higher local wound concentrations than systemic (Halasz, Arch Surgery 1977). Topical vancomycin applied to the cut edges of sternum during cardiac surgery results in decreased sternal wound infections (Vander Salm, J Thoracic and Cardiovascular Surgery, 1989). This prospective, randomized clinical trial examined 416 patients and found that the rate of sternal infection decreased by a factor of 7 in individuals who were randomized to topical vancomycin. This represents statistical significance ($p=0.02$).

Medical literature supports aggressive preventative measure as published reports state that mortality associated with sternal wound infection range from 14–47%. The average cost of individuals with sternal infections is estimated at three times the costs of the original cardiac surgery. Individuals who survive usually require prolonged hospitalization, additional surgical procedures and consequently additional complications and debilities.

What is needed is a haemostatic paste composition that avoids the disadvantages of the pre-existing haemostatic compositions discussed above, that is easily handled by doctors and medical professionals, that readily adheres to cut bone surfaces or open bone fractures, that provides an effective level of haemostasis, that has no systemic or local adverse effect and that provides bacteriostatic and bacteriocidal protection.

SUMMARY OF THE INVENTION

Accordingly, the present invention is a haemostatic paste composition comprising powdered vancomycin mixed with a biocompatible carrier. The haemostatic paste composition is easily handled, adheres well to a cut bone surface or exposed bone surface, has no systemic or local adverse effect and provides effective haemostasis to prevent blood loss from cut bone surfaces or exposed bone surfaces. The present invention is well suited for sternotomy incisions, but can be used on most cut bone surfaces or exposed bone surfaces. The vancomycin component of the present invention also provides antibiotic protection against gram-positive bacteria, such as Streptococci, Staphylococci, Clostridia, Corynebacteria and Listeria monocytogenes.

Vancomycin is a tricyclic glycopeptide antibiotic which interferes with bacterial cell wall synthesis in multiplying organisms. Vancomycin is particularly used in the treatment of severe staphylococcal infections where other antibiotics cannot be used due to patient intolerance or bacterial drug resistance.

In the preferred embodiment, 1 gram of powdered vancomycin is transferred to a sterile mixing vessel, such as a disposable medicine cup, medicine glass or small kidney basin. A volume of biocompatible carrier is then added to the sterile mixing vessel and the composition stirred with a sterile mixing instrument. Sterile water or saline solution (0.9% saline concentration) is the preferred biocompatible carrier. However, in alternate embodiments other biocompatible carriers may be used. The ratio of the powdered vancomycin to the biocompatible carrier is preferably 1:1 (gram weight:cubic centimeter volume). In alternate embodiments, the volume of biocompatible carrier may vary up to 20%, depending on the accuracy of the instrument used to measure the volume of the biocompatible carrier, to compensate for atmospheric humidity and to adjust for the thickness of the paste. The composition is stirred until the powdered vancomycin is homogenized with the biocompatible carrier. In prototype development, the length of time to homogenize the composition was one to two minutes. The resulting composition has a thick paste consistency. The presence of residual powdered vancomycin remaining in the vancomycin haemostatic paste composition does not hinder the effectiveness of the present invention.

The powdered vancomycin of the preferred embodiment was obtained from commercially available vancomycin hydrochloride. Commercially available vancomycin hydrochloride is typically distributed in sterile "flip top" vials containing lyophilized powdered vancomycin hydrochloride, wherein the vancomycin base is equivalent to either 500 milligrams or 1 gram. Although powdered vancomycin hydrochloride is preferred, any commercially available pharmaceutical grade powdered vancomycin may be used.

In the preferred embodiment, the homogenization of the powdered vancomycin and biocompatible carrier is performed in the operation room just prior to use. The haemostatic paste composition of the present invention is relatively stable at room temperature for short periods of time. The haemostatic paste composition contains no additional bacteriostatic component and is intended for immediate single dose application.

The preferred mixing instrument is a sterile wooden tongue blade; however any commercially available sterile instrument may be used. It is preferable that the mixing instrument also be used to apply the haemostatic paste composition to the cut bone surface or exposed bone surface. Alternatively, the haemostatic paste composition may be applied by hand force by a doctor or other appropriate medical professional or applied by a second sterile instrument to the cut bone surface or exposed bone surface.

It is anticipated that any quantity of powdered vancomycin may be used in preparing the haemostatic paste composition in order to adjust for the amount of paste required for a specific application. In other embodiments of the invention, the amount of powdered vancomycin used in preparing the haemostatic paste composition varied from 1 gram to 3 grams. The ratio of powdered vancomycin to biocompatible carrier remained 1:1 (gram weight to cubic centimeter volume).

DETAILED DESCRIPTION OF THE INVENTION

Accordingly, the present invention is a haemostatic paste composition comprising powdered vancomycin mixed with a biocompatible carrier that is easily handled, adheres to a cut bone surface or exposed bone surface, provides for effective haemostasis to prevent blood loss from cut bone surfaces or open bone fractures and has no systemic or local adverse effect. The present invention is well suited for use with sternotomy incisions, but can also be used on most cut bone surfaces or exposed bone surfaces. The vancomycin also provides antibiotic protection against gram-positive bacteria.

The use and preparation of vancomycin as an antibiotic agent is well known in the art. Vancomycin is a tricyclic glycopeptide antibiotic which interferes with bacterial cell wall synthesis in multiplying microorganisms. Vancomycin is active against gram-positive bacteria, such as Streptococci, Staphylococci, Clostridia, Corynebacteria and Listeria monocytogenes. Vancomycin is particularly used in the treatment of severe staphylococcal infections where other antibiotics cannot be used due to patient intolerance or bacterial drug resistance. Commercially available powdered vancomycin is typically reconstituted in sterile water and the resulting solution is administered intravenously. Although the uses of vancomycin as an antibiotic are well known, the use of vancomycin as a haemostatic agent is novel.

In the preferred embodiment of the present invention, powdered vancomycin is mixed with a volume of biocompatible carrier to form a paste that is used to stop bleeding from cut bone surfaces or exposed bone surfaces. In the preferred embodiment, 1 gram of powdered vancomycin is transferred into a mixing vessel. One cubic centimeter (milliliter) of biocompatible carrier is added to the mixing vessel and the composition mixed with a mixing instrument until the powdered vancomycin has homogenized with the biocompatible carrier. Sterile water or normal saline solution (0.9% saline concentration) is the preferred biocompatible carrier. In prototype development, the length of time to homogenize the composition was one to two minutes. The resulting composition has a thick paste consistency. The haemostatic paste composition of the present invention contains no additional bacteriostatic component, thus it is intended for immediate use. The preferred embodiment of the haemostatic paste composition is intended for effective haemostasis in sternotomy incisions, however, the present invention can be used for any cut bone surface or exposed bone surface.

In the preferred embodiment, the powdered vancomycin was obtained from commercially available vancomycin hydrochloride. Commercially available vancomycin hydrochloride is typically distributed in sterile "flip top" vials containing lyophilized powdered vancomycin hydrochloride, wherein the vancomycin base is equivalent to either 500 milligrams or 1 gram. Although powdered vancomycin hydrochloride was used in the preferred embodiment, any commercially available pharmaceutical grade powdered vancomycin may be used. In the preferred embodiment, the sterile flip top vial was opened and its contents transferred to the mixing vessel.

In the preferred embodiment, the ratio of the powdered vancomycin to the biocompatible carrier was 1 to 1 (gram weight to cubic centimeter volume). In alternate embodiments, the volume of the biocompatible carrier may vary by up to 20%, depending on the accuracy of the instrument used to measure the volume of the biocompatible carrier, to compensate for atmospheric humidity and to adjust for the thickness of the paste.

Although sterile water or normal saline solution was used as the biocompatible carrier in the preferred embodiment of the present invention, other biocompatible carriers, such as Lactated Ringers and one-half normal saline may be used in preparing the vancomycin haemostatic paste composition. In prototype development, the presence of residual powdered vancomycin remaining in the vancomycin haemostatic paste composition did not hinder the effectiveness of the present invention.

In the preferred embodiment, the thickness of the haemostatic paste composition is such that the composition is easily spread on the cut bone surfaces or exposed bone surface to stop bleeding. If the haemostatic paste composition of the present invention contains an excessive amount of the biocompatible carrier, the haemostatic paste composition will not adhere to the bone surface nor have the density to stop bleeding. If the haemostatic paste composition of the present invention does not contain a sufficient amount of biocompatible carrier, the haemostatic paste composition will contain excess powdered vancomycin which minimizes the ability of the paste to adhere to the bone surface.

In the preferred embodiment, the homogenizing of the vancomycin powder and the biocompatible carrier to form the haemostatic paste composition is performed in the operating room just prior to use. The haemostatic paste composition of the present invention is relatively stable at room temperature for short periods of time. However, the haemostatic paste composition of the present invention contains no additional bacteriostatic component and is intended for immediate single dose application. In prototype development, the haemostatic paste composition became granular in appearance when exposed to air and loses moisture.

In the preferred embodiment, the mixing vessel and the mixing instrument were sterilized prior to use in the operating room. The preferred mixing vessel is a sterile disposable medicine cup; however, any commercially available sterile container may be used such a medicine glass, small kidney basin or any small sterile cup or dish.

The preferred mixing instrument is a sterile wooden tongue blade; however, any commercially available sterile instrument may be used, such as a metal spatula, knife handle, Freer Elevator or forceps. It is preferred that the mixing instrument also be used to apply the haemostatic paste composition to the cut bone surface or exposed bone surface; however a second sterile instrument may be used to apply the haemostatic paste composition to the cut bone surface or exposed bone surface. The haemostatic paste composition may also be applied by hand force to the cut bone surface or exposed bone surface by a doctor or other appropriate medical professional.

In other preferred embodiments of the invention, the amount of powdered vancomycin used in preparing the haemostatic paste composition varied from 1 gram to 3 grams. The ratio of the powdered vancomycin to the biocompatible carrier remained the same, 1 to 1 (gram weight to cubic centimeter volume). The amount of the biocompatible carrier used in these other preferred embodiments may vary by up to 20% to adjust for the accuracy of the instrument used to measure the volume of the biocompatible carrier, to compensate for atmospheric humidity and to adjust for the thickness of the paste. It is anticipated that any quantity of powdered vancomycin may be used in preparing the haemostatic paste composition in order to adjust for the amount of paste required for application to the cut bone surface or exposed bone surface.

The vancomycin paste is not removed from the cut bone surface or exposed bone prior to closing the surgical site. The paste forms a caramelized-like coating after prolonged contact with the cut bone or exposed bone surface. This caramelized-like coating results from the interaction between the vancomycin paste with blood and other body fluids. Vancomycin is known to diffuse from one physiologic compartment to another, e.g., intravenous vancomycin can be found in the pulmonary secretions and spinal fluid in patients with meningitis. In the present invention, the vancomycin is presumed to be excreted in an unaltered form in urine.

Due to the known pharmaceutical activity of vancomycin, the haemostatic paste composition of the present invention also provides antibiotic protection against gram-positive bacteria. Vancomycin, a tricyclic glycopeptide antibiotic which interferes with bacterial cell wall synthesis in multiplying microorganisms, is active against gram-positive bacteria, such as Streptococci, Staphylococci, Clostridia, Corynebacteria and Listeria monocytogenes. Vancomycin is particularly used in the treatment of severe staphylococcal infections where other antibiotics cannot be used due to patient intolerance or bacterial drug resistance. Commercially available powdered vancomycin is typically reconstituted in sterile water and the resulting solution is administered intravenously.

Prophylactic topical vancomycin has been proven to prevent sternal wound infections in individuals undergoing sternotomy incisions for cardiac surgery. Topical antibiotics have been demonstrated to achieve much higher local wound concentrations than systemic (Halasz, Arch Surgery 1977). Topical vancomycin applied to the cut edges of sternum during cardiac surgery results in decreased sternal wound infections (Vander Salm, J Thoracic and Cardiovascular Surgery, 1989). This prospective, randomized clinical trial examined 416 patients and found that the rate of sternal infection decreased by a factor of 7 in individuals who were randomized to topical vancomycin. This represents statistical significance (p=0.02).

Medical literature supports aggressive preventative measure as published reports state that mortality associated with sternal wound infection range from 14–47%. The average cost of individuals with sternal infections is estimated at three times the costs of the original cardiac surgery. Individuals who survive usually require prolonged hospitalization, additional surgical procedures and consequently additional complications and debilities.

EXAMPLE

In clinical research and development studies, the vancomycin haemostatic paste of the present invention was used as the haemostatic agent in 500 patients undergoing sternotomy incisions. The vancomycin paste successfully occluded bleeding from the cut sternum during the surgical procedure in all 500 patients. Supplemental haemostatic agents were not required during the surgical procedure. In addition, only 1 patient developed infection of the site of the sternotomy incision. These studies also showed that the preparation of the vancomycin haemostatic paste was easily replicated and that the paste was easy to apply to the cut sternum.

The preferred embodiments described herein are illustrative only, and although the examples given include much specificity, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

What is claimed is:

1. A haemostatic composition consisting of:
a quantity of powdered vancomycin homogenized with a quantity of biocompatible carrier to form a paste for use on a cut bone surface or an exposed bone surface, the paste and the quantity of biocompatible carrier is in a ratio of 1 to 1, gram weight to cubic centimeter volume, the quantity of powdered vancomycin provides an effective amount of haemostasis and provides antibacterial protection against gram-positive bacteria.

2. The haemostatic composition of claim 1, wherein the quantity of biocompatible carrier is selected from the group consisting of sterile water, aqueous saline solution and Lactated Ringers.

3. The haemostatic composition of claim 1, wherein the paste has a spreadable consistency and adheres to the cut bone surface or the exposed bone surface.

4. A haemostatic composition consisting of:

An admixture of a quantity of powdered vancomycin and a quantity of biocompatible carrier for use on a cut bone surface or an exposed bone surface, the ratio of the quantity of powdered vancomycin to the quantity of biocompatible carrier is 1 to 1, gram weight to cubic centimeter volume, the admixture provides an effective amount of haemostasis and provides antibacterial protection against gram-positive bacteria, the quantity of biocompatible carrier being selected from the group consisting of sterile water, aqueous saline solution and Lactated Ringers.

5. The haemostatic composition of claim 4, wherein the admixture forms a paste, the paste having a spreadable consistency and adheres to the cut bone surface or the exposed bone surface.

6. A haemostatic composition consisting of:

a quantity of powdered vancomycin homogenized with a quantity of biocompatible carrier to form a paste for use on a cut bone surface or an exposed bone surface, the paste having a spreadable consistency and adheres to the cut bone surface or the exposed bone surface to provide an effective amount of haemostasis, the quantity of powdered vancomycin additionally providing antibacterial protection against gram-positive bacteria, the quantity of powdered vancomycin and the quantity of biocompatible carrier being in a ratio of 1 to 1, gram weight to cubic centimeter volume.

7. The haemostatic composition of claim 6, wherein the quantity of biocompatible carrier is selected from the group consisting of sterile water, aqueous saline solution and Lactated Ringers.

* * * * *